United States Patent [19]

Steer

[11] Patent Number: 4,883,477

[45] Date of Patent: Nov. 28, 1989

[54] OSTOMY APPLIANCE

[75] Inventor: Peter L. Steer, Surrey, England

[73] Assignee: E. R. Squibb and Sons, Inc., Princeton, N.J.

[21] Appl. No.: 182,274

[22] Filed: Apr. 15, 1988

[30] Foreign Application Priority Data

May 22, 1987 [GB] United Kingdom ............... 8712190

[51] Int. Cl.⁴ .............................................. A61F 5/44
[52] U.S. Cl. ................................................ 604/339
[58] Field of Search ............................. 604/332–345

[56] References Cited

U.S. PATENT DOCUMENTS 2,148,716 6/1985 Steer .
8,503,247 8/1985 Edwards ............................ 604/342

Primary Examiner—Jerome L. Kruter
Attorney, Agent, or Firm—Donald J. Barrack; Robert E. Lee, Jr.

[57] ABSTRACT

An ostomy appliance has four annular parts. The first part is attachable to the body of the wearer. It is also attachable to the third part by a second part which comprises a rotatable locking ring. The third part is attachable to the fourth part in a push fit manner and the ostomy bag is connected to the fourth part.

4 Claims, 4 Drawing Sheets

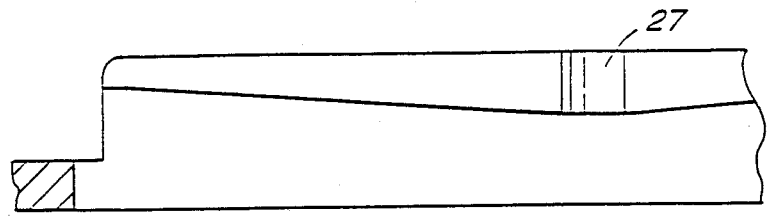
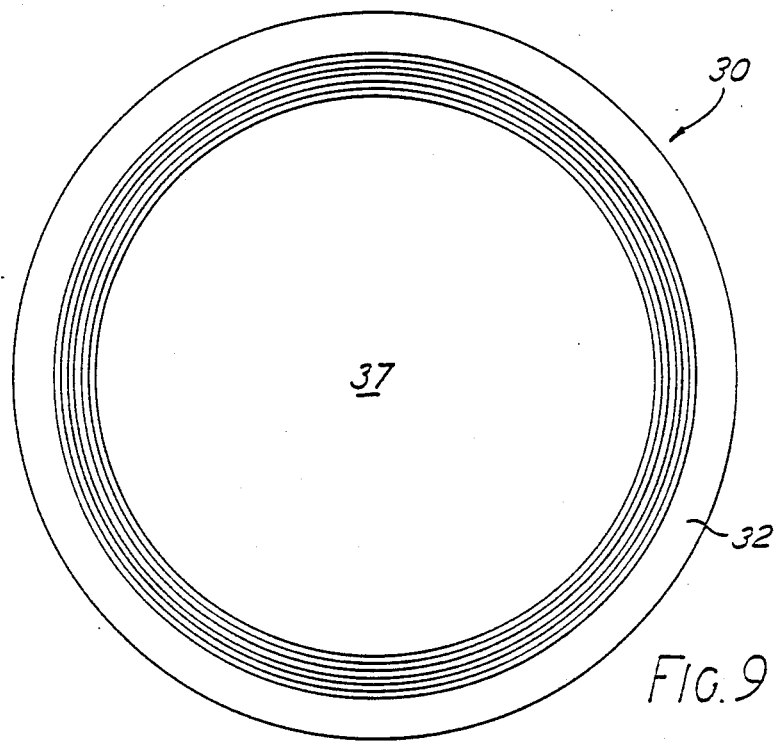
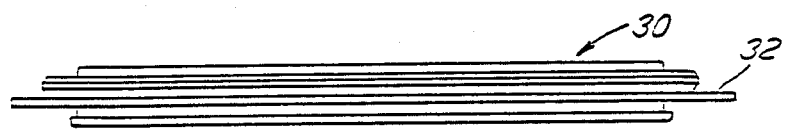

OSTOMY APPLIANCE

BACKGROUND OF THE INVENTION

A commercially successful two-piece ostomy system having a body side with a coupling element adapted to mechanically engage a coupling element affixed to an ostomy pouch is described by Steer et al. in U.S. Pat. No. 4,460,363 and United Kingdom Patent No. 1,571,657.

Another commercially available system in order to minimize pressure against the body when a new pouch is affixed to the body side provides a flexible plastic web between the adhesive pad and the body side coupling element as shown by Alexander in U.S. Pat. No. 4,419,100 and United Kingdom Patent No. 2,115,288B. This is also shown by Hunger in European Patent Application No. 94,613. Another commercially available system employs an accordion element between the adhesive pad and the body side coupling element as shown by Jensen in European Patent Application No. 98,718. Steer in U.S. Pat. No. 4,710,183 and United Kingdom Patents Nos. 2,148,716B and 2,179,556B discloses a version of the commercial system described above wherein a flexible chute ring is interposed between the body side coupling element and the adhesive pad. Steer et al. in United Kingdom Patent Application No. 2,119,654A describe another embodiment wherein the body side coupling element has a lateral flange angled away from the adhesive pad and an applicator is inserted between the angled portion of the flange and the pad. Arnone et al. in U.S. Pat. No. 4,642,107 employ a separate accordion element between the body side and bag side coupling element described in the Steer et al. commercial device. Ferguson in U.S. Pat. No. 4,664,661 discloses a modified version of the accordion system and in U.S. Pat. Nos. 4,648,875 and 4,685,990 employs a polymeric foam between the adhesive pad and body side coupling element.

Edwards et al. in U.S. patent application No. 2,181,652A disclose an ostomy appliance wherein the body side coupling element is spaced from the adhesive pad by a stiff or semi-rigid stepped support member. Edwards in PCT Application No. WO/85/03427 and United Kingdom Patent Application No. 2,190,841A discloses as ostomy appliance including a rotatable belt attaching ring. Edwards in United Kingdom Patent Application No. 2,193,893A disclose an ostomy appliance having mechanically fitting body side and bag side coupling elements.

Steer et al. in United Kingdom Patent No. 1,568,860 disclose an ostomy appliance wherein the body side includes a deflectable seal strip and the bag and body side elements are joined by Velcro. Steer et al. in United Kingdom Patent No. 1,579,875 disclose an ostomy appliance wherein a bayonet-type coupling is employed. Steer et al. in United Kingdom Patent No. 2,121,902B disclose an ostomy appliance wherein the body side coupling element consists of a flange having an inner wall and a series of projecting members spaced from one another peripherally and radially spaced from the inner wall and a bag coupling including a rib with a deflectable sealing strip. Steer in United Kingdom Patent Application No. 2,163,350A discloses an ostomy appliance wherein the body side coupling element is of a V-formation adapted to fit within a channel shaped coupling element on the ostomy bag. Steer in United Kingdom Patent Application No. 2,173,403A discloses an ostomy appliance wherein the V-shaped body side coupling member is telescopically slidable to provide access for the fingers of the user beneath the V-shaped portion. Steer in United Kingdom Patent Application No. 2,183,481A discloses an ostomy appliance including an inner chute member. Steer et al. in Unite Kingdom Patent Application No. 2,193,098A disclose a three part ostomy appliance wherein the body side has a flange, a central chute, and an array of space projections, the bag coupling element has a deflectable seal strip for engaging and surrounding the outer wall of the chute and a projecting rim which can be snap fitted on the space projections, and a third part rotatable to effect a positive lock between the rim and the projections. Steer et al. in U.S. Pat. No. 4,518,389 disclose an ostomy appliance wherein an interdigitation of pins and heads secure the coupling elements. Steer in U.S. Pat. No. 4,559,048 discloses an ostomy appliance wherein the coupling includes an annular ring constructed to be snap-fitted to the body side coupling element so that the user can place his thumbs under the ring to support the body side coupling element against inwardly-directed forces applied when fitting a new bag.

Other two-piece mechanically joined ostomy appliances are disclosed by Schneider et al. in U.S. Pat. No. 4,610,676, by Mohiuddin in U.S. Pat. No. 4,610,677, by Oczkowski in U.S. Pat. No. 4,359,051, by Hauer in European Patent Application No. 163,979, by Johns in European Patent Application No. 251,502, and by Kay in United Kingdom Patent Application No. 2,193,439A.

SUMMARY OF THE INVENTION

This invention relates to a coupling system for use in attaching an ostomy appliance to a wearer.

It is an aim of the present invention to provide an improved ostomy appliance of the type which has interengagable coupling elements, one of which (herein called the body side coupling element) is, or can be, secured to a medical grade adhesive pad and another of which is, or can be, secured to an ostomy bag.

According to one aspect of the present invention, there is provided an ostomy appliance which is made up of four annular parts of which a first part is attached to the body of the wearer by a pad of medical grade adhesive and is also attachable to a third part by a second part comprising a rotatable locking ring, and the third part is itself attachable to the fourth part in a push-fit manner, the fourth part being connected to the ostomy bag.

In the use of such an arrangement, firstly the fourth part (the bag side coupling ring) and the third part are snapped together while both these parts are separate from the first and second parts. The second part (the rotatable locking ring) is made captive to but is rotatable relative to the third part. The first part is attached to the wearer by the medical grade adhesive. The second, third and fourth parts thus pre-assembled before being presented to the first part and hence no pressure can be communicated to the tender peristomal area. The second part comprising the locking ring is then rotated to its unlocked position and the connected third and fourth parts are then brought up to the first part, gently slid thereon, and the second part is rotated to its locked position.

BRIEF DESCRIPTION OF THE DRAWINGS

The invention will be better understood from the following non-limiting description of an example thereof given with reference to the accompanying drawings in which:

FIG. 8 is a view on the arrow A (FIG. 7) of a portion of the second part showing a detent recess; and FIGS. 9 and 10 are respectively front and side elevation views of the third part shown in FIG. 3, on a smaller scale than FIG. 3.

DETAILED DESCRIPTION OF THE INVENTION

Figure 1:
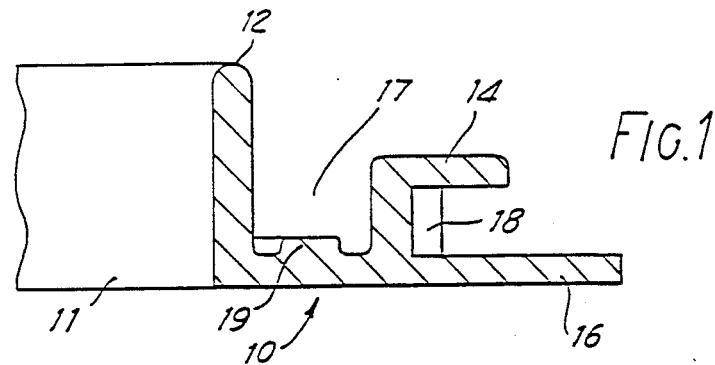
FIGS. 1–4 show respectively, in crosssections taken in a radial plane, one example of each of the first, second, third and fourth parts of one example of coupling ring according to the invention.
Figure 6:
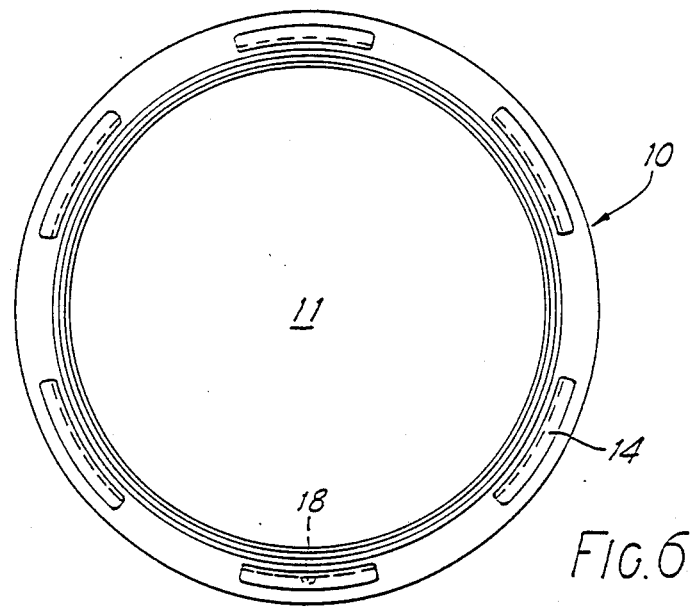
FIG. 6 is an elevation view of the first part shown in FIG. 1.

Referring firstly to FIGS. 1 and 6, the illustrated first part 10 includes a substantially cylindrical chute wall 12 encircling a stomal aperture 11, and a flange 16 extends radially outward from one end of the chute wall 12. The flange 16 carries a series of arcuately spaced hook portions 14. These hook portions are equally arcuately spaced around the center of the stomal aperture. As illustrated, there are six hook portions 14 and they are located at 60° centers. Each one subtends on angle of 30° at the center. However, it is not essential to employ six hook portions nor is it essential that they should be equally arcuately spaced providing the spacing is chosen so that interlocking as a result of relative rotation is possible. This will be better understood after a consideration of the later part of this description.

Figure 5:
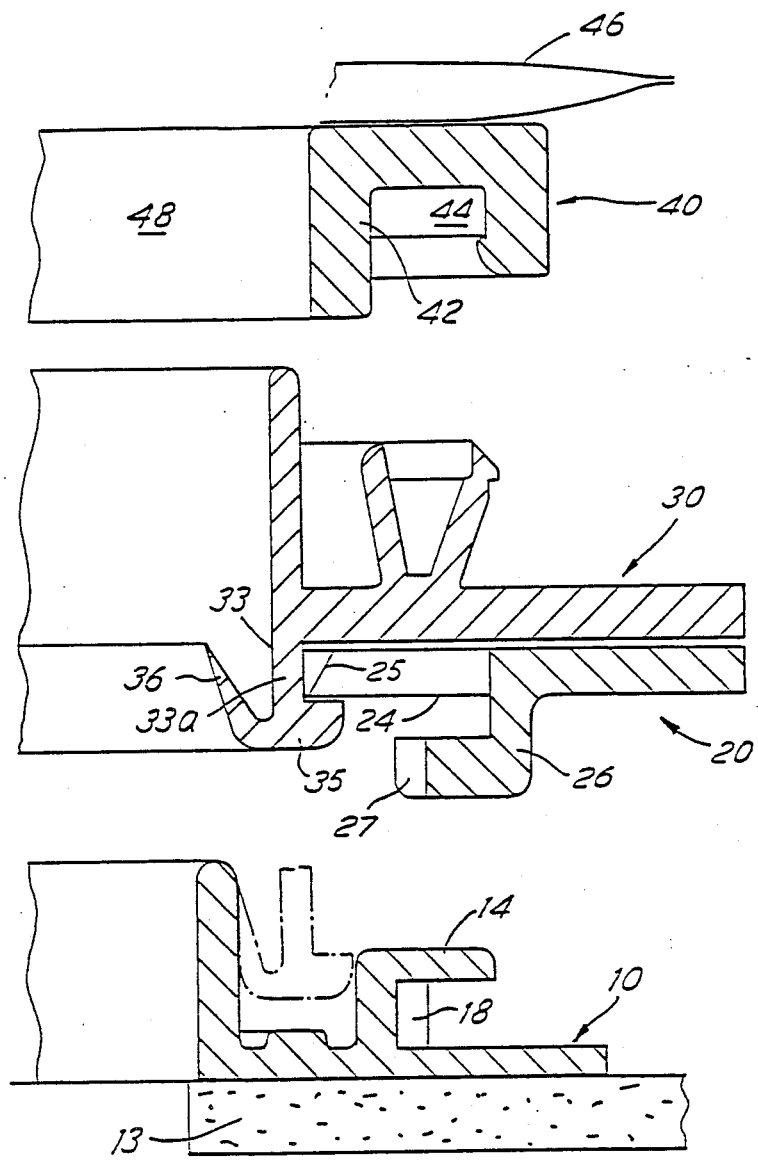
FIG. 5 is a similar cross-sectional view showing the manner of assembly of the parts illustrated in FIGS. 1–4.

A channel 17 is located radially outwardly of the chute wall 12 and radially inwardly of the hook formations 14. The purpose of this channel 17, as seen from the lower part of FIG. 5, is to receive portions of the third part 30.

Figure 2:
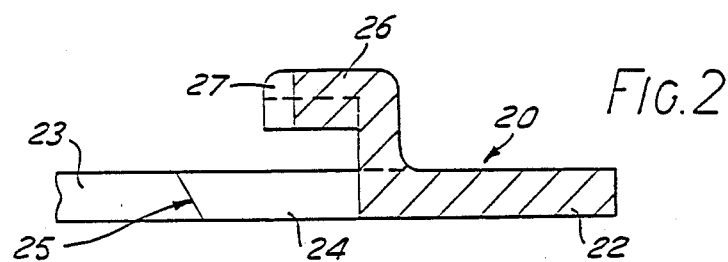
Figure 7:
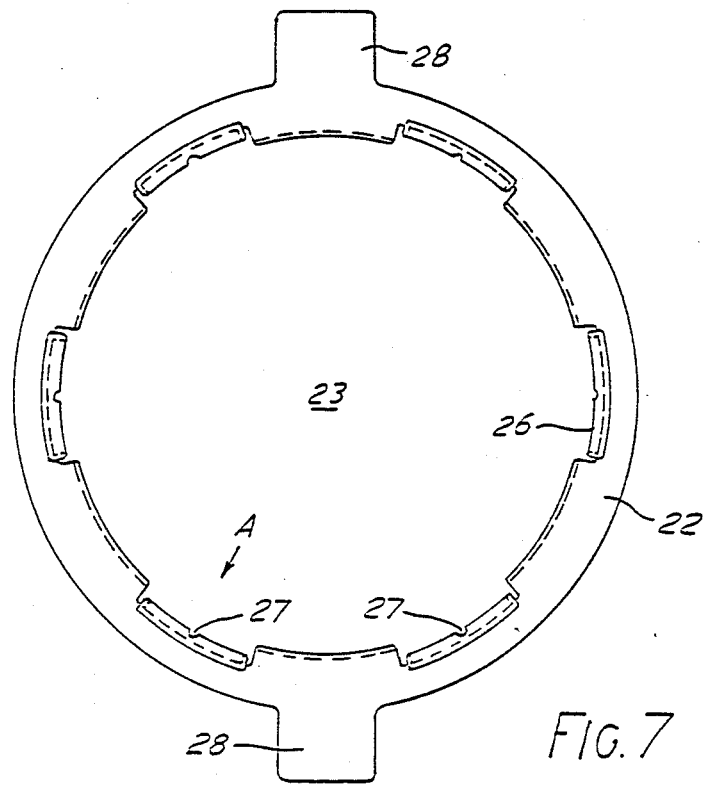
FIG. 7 is an elevation view of the second part shown in FIG. 2.

Referring now to FIGS. 2, 7 and 8 the illustrated second part 20 is generally annular in shape and has an encircling flange 22 which at certain locations has extensions 24 projecting radially inwardly and at other locations has hook portions 26. The inner edge of each extension 24 is chamfered as seen at 25, and a stomal aperture is illustrated at 23. Each of the hook portions has a recess 27 therein, for co-operation with a detent as will be later described.

The flange 22 has extending radially therefrom a pair of radial arms 28. These serve as handles or gripping portions enabling a manual rotation of the second part 20 in relation to the first part 10. As seen best in the lower part of FIG. 5, the hook portions 26 of the second part 20 extend into a recess defined by the hook portions 14 and flange 16 of the first part 10. As illustrated, each hook portion 26 subtends an angle of 26° at the center, and the hook portions 26 are located at centers angularly spaced at 60°. It will be apparent to a man of average skill in the art that a different number of hook portions and a different angular spacing could be employed if appropriate changes were made in the first part 10. It will be understood that by relative rotation between the first and second parts 10, 20, the hook portions 26 can be shifted between respective locking and unlocking positions. In the relative locked position the parts 10 and 20 are prevented from axial separation by overlapping of the hook portions 26 with the hook portions 14, whereas in the unlocked relative rotational positions the two parts can be separated.

Figure 3:
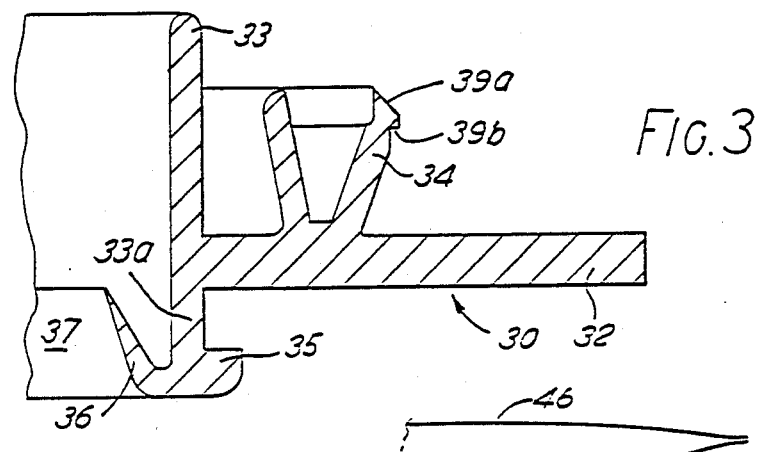

Referring now to FIGS. 3, 9 and 10, the illustrated third part 30 includes a radially outwardly extending annular flange 32 and a substantially cylindrical chute wall 33. This has an extension wall 33a which carries a radially outwardly located hook formation 35 and a radially inwardly located integral deflectable sealing strip 36. In connection with this sealing strip, reference may be had to British Patent No. 1 568 860. As shown in FIG. 5, hook formation 35 and seal strip 36 are dimensioned to fit within channel 17 such that the seal strip is deflected towards wall 33 and springs outwardly to engage chute wall 12 in a gas and fluid tight manner.

The flange 32 carries a peripherally extending V-shaped coupling member 34. The outer rib portion of the V-shaped coupling member includes a step-formation 39b and a beveled edge 39a. The part 30 encircles a stomal aperture 37 which of course is aligned, in use, with the stomal apertures 11, 23, and 48.

Figure 4:
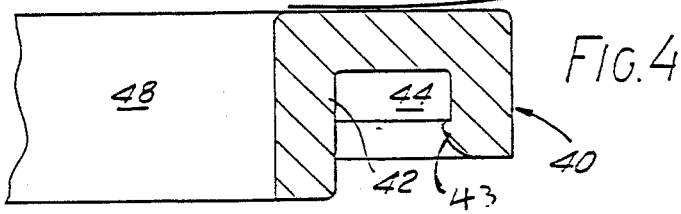

Referring now to FIG. 4, the fourth part is formed by a coupling ring 40 which, as illustrated, is shown attached to an ostomy bag 46. This attachment may be by plastics welding, for example, or by adhesive. The coupling ring 40 has a radially inner wall 42 which defines with the remainder of the ring 40 a channel 44. When the fourth part 40 is joined to the third part 30 as shown in FIG. 5, V-shaped coupling member 34 fits within channel 44 and rim 43 contacts step-formation 39b.

In use the first part is usually attached to the body of the wearer by a pad of medical grade adhesive 13, see FIG. 5. Suitable adhesive compositions are taught by Chen in U.S. Pat. No. 3,339,546, by Chen et al. in U.S. Pat. No. 4,192,785, by Pawelchak et al. in U.S. Pat. No. 4,393,080, or by Doyle et al. in U.S. Pat. No. 4,551,490. The body contacting surface of the adhesive pad is usually covered by a sheet of release paper prior to use. An aperture is provided in the pad 13 which the user can enlarge to fit snuggly around the stoma. Of course, the stomal opening can not extend as far as aperture 11 in the first part 10. The non-body contacting surface of adhesive pad 13 will normally be covered with a thin polymeric film to which part 10 can be affixed by heat sealing, welding, or by adhesive. The second part 20 is secured to the third part 30 by urging the extension 24 of the second part over the peripheral hook formation 35 of the third part 30. The chamfered inner edges 25 of the extensions 24 assists this operation. In this manner the second part 20 is rotatably yet securely attached to the third part 30. The fourth part is then secured to the assembled second and third parts by urging the V-shaped coupling member 34 into engagement with the channel 44. Having thus connected the ostomy bag 46 to the second part 20 and the third part 30, the assembled second, third and fourth parts are brought towards the first part 10 so that the parts 33a, 35 and 36 enter the channel 17 and the hook portions 26 of the second part 20 are aligned between the hook portions 14 of the first part 10. The ring 20 is then rotated into its locking position so that the hook portions 26 of the second part extend into a recess defined by the hook portions 14 and flange 16 of the first part 10, thus securely maintaining the four parts 10, 20, 30 and 40 all connected to one another. The provision of the detent 18 on the first part 10 which co-operates with any particular one of the recesses 27 on the second part 20 gives a clear indication to the wearer that the rotation of the locking ring 20 relative to the first part 10 has been adequate to move the parts into a mutually securely coupled condition. This detent arrangement tends to hold the parts in locked position.

As described above, assembly of the second and third parts is followed by connection of the fourth part; instead the third and fourth parts may be assembled and the second part then attached. In either event, it will be understood that the illlustrated arrangement requires the pre-assembly of the second, third and fourth parts prior to connection to the first part.

The parts 10 and 30 may be made of low density, and the part 20 of high density polyethylene. The part 40 may be made of the plastics material ethylene vinyl acetate. Other materials may also be suitable for parts 10, 20, 30 and 40.

It will be understood from the above description that essentially no pressure in an axial direction need be applied to the part 10. This part is normally secured to the tender and sensitive peristomal area by the medical grade adhesive pad 13. In this way, a secure and leakproof attachment of an ostomy bag can be achieved with relatively simple manual manipulation and, importantly, without subjecting the tender peristomal area of the wearer to any significant disturbance or pressure.

What is claimed is:

1. An ostomy appliance which includes four separate annular parts of which a first part is attachable to the body of the wearer by a pad of medical grade adhesive and is also attachable to a third part by rotating a second part comprising a rotatable locking ring from a non-locking position to a locking position, the second part also being attachable to the third part, and the third part is itself attachable to the fourth part in a push-fit manner, the fourth part connected to the ostomy bag, said second, third and fourth parts being attachable as an assembly separate from attachment to said first part.

2. An ostomy appliance according to claim 1 in which the second part is made captive to but is rotatable relative to the third part.

3. An ostomy appliance according to claim 2 in which the third part includes a radially extending flange, a chute wall, and a peripherally extending coupling member which is substantially V-shaped in cross-section, and the fourth part includes a channel portion for receiving the V-shaped coupling member for attaching said third part to said fourth part.

4. An ostomy appliance according to claim 3 in which each of the four parts has a stomal aperture and the diameter of that in the first part is smaller than, and the diameter of that in the fourth part is larger than, that in the third part.

* * * * *